US00PP22571P2

(12) United States Plant Patent
Carruth

(10) Patent No.: US PP22,571 P2
(45) Date of Patent: Mar. 13, 2012

(54) FLORIBUNDA ROSE PLANT NAMED 'WEKCHARLIE'

(50) Latin Name: *Rosa hybrida*
Varietal Denomination: WEKcharlie

(75) Inventor: Thomas F. Carruth, Altadena, CA (US)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 0 days.

(21) Appl. No.: 12/927,751

(22) Filed: Nov. 22, 2010

(51) Int. Cl.
*A01H 5/00* (2006.01)

(52) U.S. Cl. ..... Plt./151

(58) Field of Classification Search ..... Plt./151
See application file for complete search history.

*Primary Examiner* — Annette Para

(57) ABSTRACT

A new variety of Floribunda rose suitable for garden decoration, having flowers of red velvet coloration.

1 Drawing Sheet

Classification: The present invention relates to a new *Rosa hybrida* plant.

Variety denomination: The new plant has the varietal denomination 'WEKcharlie'.

BACKGROUND OF THE INVENTION

This invention relates to a new and distinct variety of Floribunda Rose. It has as its seed parent the variety known as 'WEKsanpoly' (U.S. Plant Pat. No. 13,513) and as its pollen parent the variety known as 'ADHarman' (not patented).

SUMMARY OF THE INVENTION

Among the features which distinguish the new variety from other presently available and commercial rose cultivars known to the inventor are the following combinations of characteristics: its hairy peduncle and flower receptacle, its red suffusion on the inner surface of the sepal that appears as the flower ages, its very glossy foliage and its red velvet flower coloration that lasts throughout the life of the flower. The plant has a moderately upright compact and rounded growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKcharlie' may be asexually propagated by cuttings, budding and grafting. The budding and grafting successfully occurred on the plant/rootstock *Rosa hybrida* cv. 'Dr. Huey' (not patented).

Comparison with Parents

The new rose may be distinguished from its seed parent, 'WEKsanpoly' by the following combination of characteristics: whereas 'WEKcharlie' bears large sized flowers (about 8.5 to about 12.3 cm. in diameter), 'WEKsanpoly' bears significantly smaller flowers (about 6.5 to about 9.0 cm. in diameter). The new variety has a moderately upright compact and rounded growing habit (about 60 to about 70 cm. spread at the widest point), whereas the seed parent has a significantly more spreading rounded bushy to somewhat upright growing habit (about 72 to about 88 cm. spread at the widest point).

The new variety may be distinguished from its pollen parent, 'ADHarman' by the following combination of characteristics: whereas 'WEKcharlie' bears double flowers (about 20 to 26 petals) of red velvet coloration, 'ADHarman' bears flowers of dusky red coloration with significantly heavier petalage (about 24 to 34 petals). The new variety bears flowers with a slight tea fragrance, whereas the pollen parent bears flowers with a strong fruity and rich rose fragrance.

Comparison with the Closest Commercially Available Cultivar

The new variety may be distinguished from its closest commercially available cultivar, 'POUlman' (U.S. Plant Pat. No. 6,264) by the following combination of characteristics: whereas 'WEKcharlie' bears large sized (about 8.5 to about 12.3 cm. in diameter) double flowers (about 20 to 26 petals), the closest commercially available cultivar bears significantly smaller flowers (about 8.0 to about 10.0 cm. in diameter) with significantly heavier petalage (about 30 to 35 petals).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

Flower

The new variety usually bears its flowers singly, sometimes in clusters of two to three per stem. Flowers may be borne in regular rounded clusters on strong short to medium length stems (about 21 to about 54 cm.). Outdoors, the plant blooms abundantly and nearly continuously during the growing season. The flowers have a slight tea fragrance.

Bud

The peduncle is about 3.6 to about 7.7 cm. in length, of somewhat heavy caliper (about 0.3 to about 0.4 cm. in diameter), and usually erect. It is moderately rough, with some stipitate glands and hairs. Peduncle color is between 146C and 146B often moderately suffused, especially on the side exposed to the sun, with between 183A and 187B.

Before the calyx breaks, the bud is about 1.5 to about 1.8 cm. in diameter at the widest point, about 1.5 to about 2.2 cm. in length, and pointed to somewhat ovoid in shape. The surface of the bud bears between 6 to 8 foliaceous appendages and few hairs, usually with moderately stout much cut foliaceous parts extending beyond the tip of the bud about ½ or more of its length. Bud color is between 137B and 146B often moderately suffused, especially on the side exposed to the sun, with between 187B and 187A.

The sepals are about 2.6 to about 3.7 cm. in length and about 0.6 to about 1.2 cm. in width at the widest point. The outer surface color of the sepal is between 137B and 146B often moderately suffused, especially on the side exposed to the sun, with between 187B and 187A. The inner surface color of the sepal is near 146C broadly bordered by near 137A. After the sepals open, the inner surface color is often heavily suffused, especially on the area exposed to the sun, with between 187A and 187B. The inner surface of the sepal is covered with fine wooly tomentum; sepal margins are lined with some hairs and sometimes very few stipitate glands.

The receptacle of the flower is of medium length (about 0.5 to about 0.7 cm.) and somewhat heavy in caliper (about 0.7 to about 0.9 cm. in diameter). The receptacle is urn-shaped in form. Its surface is very smooth with few hairs and with thick fleshy walls. The receptacle color is between 144A and 146B.

As the petals open (after the calyx breaks), the bud is about 1.8 to about 2.4 cm. in diameter at the widest point, about 2.5 to about 3.1 cm. in length, and ovoid in form. The color of the under surfaces of the newly opened petals is between 59A and 60A. At the point where the petal attaches, there is a somewhat small zone of between 1C and 154C. The color of the upper surfaces of the newly opened petals is between 187A and 187B. At the point where the petal attaches, there is a somewhat small zone of between 3B and 2B.

Bloom

When fully open, the bloom ranges from about 8.5 to about 12.3 cm. in diameter. Petalage is double with about 20 to 26 petals and about 0 to 3 petaloids irregularly arranged. When partially open, the bloom form is moderately high centered to somewhat cupped, and the petals are tightly spiraled to cupped with petal edges moderately reflexed outward. When fully open, the bloom form is more cupped, and the petals are loosely cupped to moderately undulated with petal edges moderately reflexed outward to somewhat rolled.

Petals

The substance of the petals is moderately heavy and of somewhat thin to medium thickness, with upper surfaces moderately satiny to somewhat velvety and under surfaces slightly shiny to matte. The petals are about 4.4 to about 5.9 cm. in length and about 3.7 to about 6.3 cm. in width at the widest point. Petal margins are entire.

The outer petals are moderately obovate to somewhat rounded in shape with rounded apices.

The inner petals are obovate to somewhat oblanceolate in shape with rounded apices.

Petaloids are about 1.9 to about 3.5 cm. in length and about 1.2 to about 2.7 cm. in width at the widest point. Petaloids are irregularly shaped moderately obovate to somewhat oblanceolate with rounded apices.

Newly Opened Flower

The under surface color of the outer, intermediate and inner petals is between 58B and 53C. At the point where the petal attaches, there is a somewhat large zone of between 4B and 5C. The upper surface color of the outer, intermediate and inner petals is between 53B and 53C sometimes suffused, especially on the outermost petal with between 187A and 187B. At the point where the petal attaches, there is a moderately large zone of between 12A and 9A.

The under and upper surface colors of the petaloids are similar in coloration to the upper and under surfaces of the intermediate and inner petals.

The general tonality of the newly opened flower is between 53B and 53C sometimes suffused, especially on the outermost petal with between 187A and 187B.

Three-Day-Old Flower

The under surface color of the outer, intermediate and inner petals is between 61B and 60B. At the point where the petal attaches, there is a somewhat large zone of between 2D and 4D. The upper surface color of the outer, intermediate and inner petals is between 53B and 53C often suffused, especially on the outermost petal with between 187A and 187B. At the point where the petal attaches, there is a moderately large zone of between 3C and 4B.

The under and upper surface colors of the petaloids are similar in coloration to the upper and under surfaces of the intermediate and inner petals.

The general tonality of the three-day-old flower is between 53B and 53C often suffused, especially on the outermost petal with between 187A and 187B.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

Male Reproductive Organs

Stamens are many in number (average about 145) and are arranged regularly about the pistils; a few are mixed with petaloids. The filaments are of somewhat long length (about 0.7 to about 1.4 cm.) most with anthers. Filaments are between 13A and 14B in color often heavily suffused with between 53B and 53C. The anthers are somewhat large for the class and all open approximately at the same time. Anther color when immature is near 20B on the external part and near 19C on the internal part. Anther color at maturity is near 163A on the external part and near 200A on the internal part. Pollen is abundant and between 20B and 18A in color.

Female Reproductive Organs

Pistils vary in number (average about 120). The styles are moderately even, somewhat short to average in length (about 0.4 to about 0.7 cm.), heavy in caliper and moderately tightly bunched. Stigma color is near 20B. Style color is between 154C and 150C usually heavily suffused with between 53A and 53B. Ovaries are usually all enclosed in the calyx.

Hips are of average length (about 1.2 to about 1.5 cm.), rounded in form with a flat top, and between 25A and 28B in color when ripe. The hip surface is very smooth with thick fleshy walls. The sepals are moderately permanent and usually straight in shape.

The seeds are irregularly rounded, smooth in texture, approximately 4 to about 9 per hip, about 0.3 to about 0.5 cm. in diameter at the widest point and between 161C and 162C in color.

Foliage

The compound leaves are usually comprised of three to five leaflets and are borne abundantly. The five-leaflet leaves are about 7.6 to about 13.8 cm. in length and about 6.2 to about 11.3 cm. in width at the widest point, moderately leathery to somewhat crisp in texture, and very glossy in finish on the upper side and matte in finish on the under side. The terminal leaflets are about 3.1 to about 7.3 cm. in length and about 1.8 to about 4.7 cm. in width at the widest point, shaped ovate with acute apices and rounded bases. Their margins are usually simply serrate.

The upper surface color of the mature leaf is between 139A and 146A. The under surface color of the mature leaf is between 147B and 146B. The upper surface color of the young leaf is between 137A and 146A, often heavily suffused with between 187B and 187A. The under surface color of the young leaf is between 147B and 146A, often heavily suffused with between 187B and 187A.

The rachis is of somewhat light caliper and moderately rough. The upper side is deeply grooved with few hairs and stipitate glands on the edges of the grooves. The under side of the rachis is moderately rough with few hairs, few stipitate glands and small prickles. The rachis color is near 146D on the under side and near 137C on the upper side, often heavily suffused on the young leaf with between 187B and 187A.

The stipules are about 1.0 to about 1.4 cm. in length and somewhat narrow to medium in width (about 0.5 to about 0.8 cm.) with moderately long straight points that usually turn out at an angle of more than 45 degrees and sometimes recurve toward the stem. The under and upper surface color of the stipule is between 146B and 137C, often heavily suffused on the young leaf with between 187B and 187A.

The petiole is of somewhat light caliper and moderately rough. The upper side is deeply grooved with few hairs and stipitate glands on the edges of the grooves. The under side of the petiole is moderately rough with few hairs, few stipitate glands and small prickles. The petiole is about 0.5 to about 1.9 cm. in length and about 0.1 to about 0.15 cm in width at the widest point. The petiole color is near 146D on the under side and near 137C on the upper side, often heavily suffused on the young leaf with between 187B and 187A.

The plant displays an average degree of resistance to powdery mildew and rust as compared to other commercial varieties grown under comparable conditions in Pomona, Calif. The plant's winter hardiness and drought/heat tolerance are yet to be determined.

Growth

The plant has a moderately upright compact and rounded medium height growing habit (about 85 to about 100 cm. in height and about 60 to about 70 cm. spread at the widest point), with full branching. It displays moderately vigorous growth and the canes are of somewhat heavy caliper for the class (about 1.5 to about 2.0 cm. in width at the widest point).

The color of the major stems is between 147B and 152A. They bear some large prickles that are about 0.5 to about 0.8 cm. in length. The large prickles are angled moderately downward with a long narrow oval base; prickle color is near 165B overlaid with 201B. The major stem bears few small prickles of similar shape and coloration.

The color of the branches is between 146A and 146B. They bear some large prickles which are of similar size and shape to the large prickles on the major stems; prickle color is between 161A and 162B sometimes lightly suffused with near 187D. The branches bear some small prickles of similar shape and coloration.

The color of the new shoots is between 146B and 146A sometimes lightly suffused with between 183B and 187B. They bear some large prickles which are of similar size and shape to the large prickles on the major stems; prickle color is between 153A and 152C often moderately suffused with between 187B and 183B. The shoots bear some small prickles of similar shape and coloration.

I claim:

1. A new and distinct Floribunda rose plant of the variety substantially as described and illustrated herein.

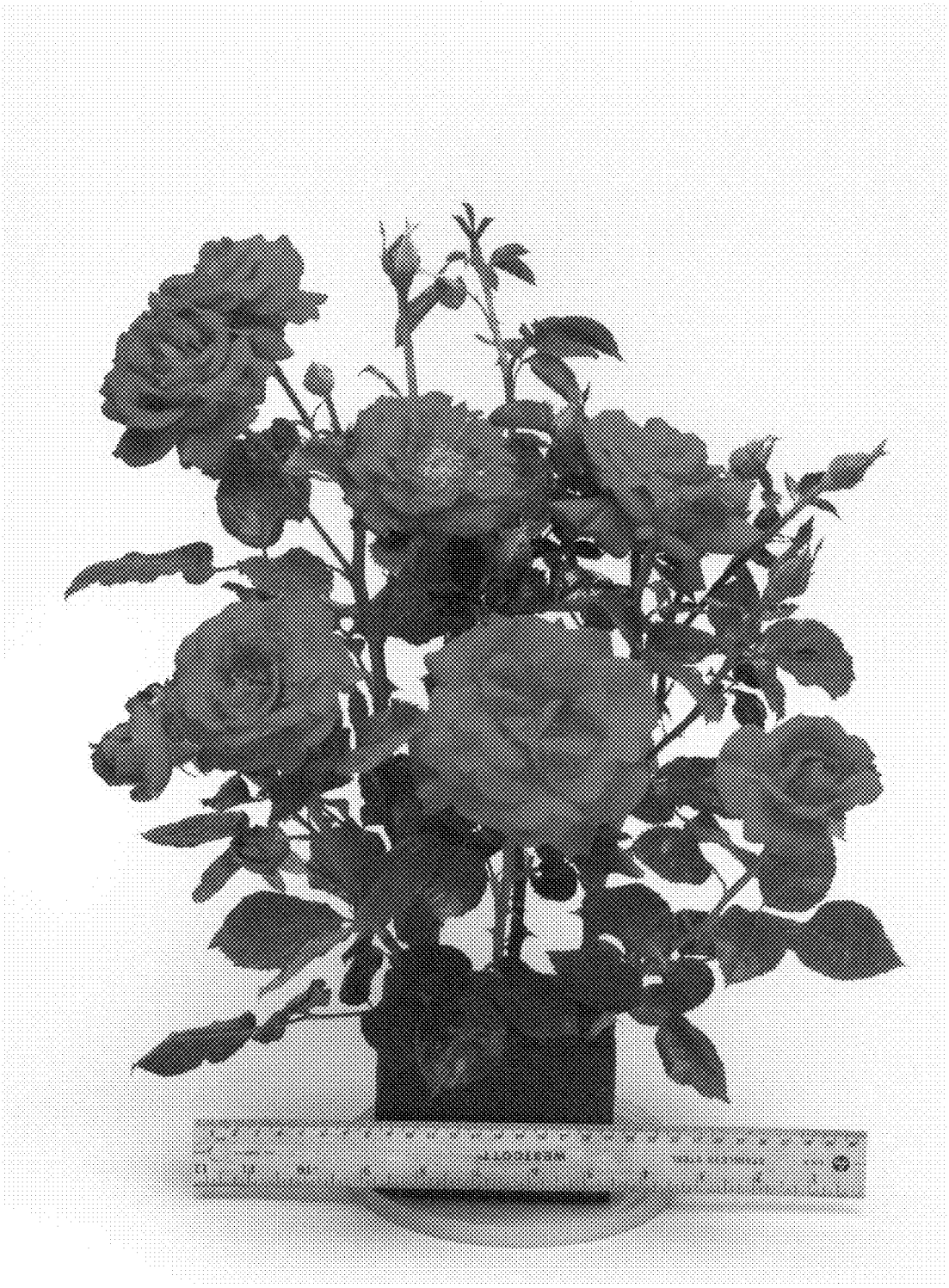

* * * * *